United States Patent [19]

Narra et al.

[11] 4,342,740
[45] Aug. 3, 1982

[54] METHOD AND KIT FOR LABELING RED BLOOD CELLS WITH TECHNETIUM-99M

[75] Inventors: Rama K. Narra, North Brunswick; Bruce L. Kuczynski, Highland Park, both of N.J.

[73] Assignee: E. R. Squibb & Sons, Inc., Princeton, N.J.

[21] Appl. No.: 179,306

[22] Filed: Aug. 18, 1980

[51] Int. Cl.³ .................. A61K 49/00; G01T 1/00; B65D 71/00
[52] U.S. Cl. .............................. 424/1; 422/61; 424/1.5; 424/9
[58] Field of Search ............. 424/1, 1.5, 9; 422/61

[56] References Cited

U.S. PATENT DOCUMENTS 3,725,295  4/1973  Eckelman et al. ............. 424/1
3,988,429  10/1976  Richards et al. .............. 424/1

OTHER PUBLICATIONS

Atkins et al., Radiology, 106: 357–360 (1973).
Hegge et al., J. Nucl. Med., 19: 129–134 (1978).
Eckelman et al., J. Nucl. Med., 12: 22–24 (1971).
Pavel et al., J. Nucl. Med., 18: 305–308 (1977).
Gutkowski et al., J. Nucl. Med. 15: 1187–1191 (1975).
Smith et al., J. Nucl. Med., 17: 126–132 (1976).
Hamilton et al., J. Nucl. Med., 17: 1038–1043 (1976).
Fouye' et al., J. Nucl. Med., 16: 435–437 (1975).
Korubin et al., J. Nucl. Med., 13: 760–762 (1972).
Eckelman et al., Am. J. Roentgenol. Radium. Ther. Nucl. Med., 118: 861–864 (1973).
Ducassou et al., Brit. J. of Radiology, 49: 344–347 (1976).
Burdine et al., Radiology, 91: 162–164 (1968).
Eckelman et al., J. Nucl. Med., 12: 310–311 (1971).
Atkins et al., J. Nucl. Med., 13: 811–814 (1972).
Smith, Int. J. Appl. Rad. Isot., 25: 137–139 (1974).

Primary Examiner—Christine M. Nucker
Attorney, Agent, or Firm—Lawrence S. Levinson; Donald J. Barrack

[57] ABSTRACT

The labeling of red blood cells with technetium-99m using a stannous reducing agent is facilitated by the addition of an oxidizing agent along with the radioactive pertechnetate ion.

13 Claims, No Drawings

METHOD AND KIT FOR LABELING RED BLOOD CELLS WITH TECHNETIUM-99M

BACKGROUND OF THE INVENTION

Red blood cells have been labeled with technetium-99m and used in nuclear medicine for red cell volume determinations, placenta localization, cardiac imaging and blood flow studies, and after heat denaturation for spleen imaging.

Both in vitro and in vivo methods have been disclosed for labeling red blood cells with technetium-99m, and both methods employ stannous ion for the reduction of the pertechnetate ion. This reduction appears to be necessary for satisfactory labeling of red blood cells. As reported in the literature, the amount of stannous ion utilized in these procedures is critical; see, for example, U.S. Pat. No. 3,988,429 and J. Nucl. Med., 18: 305-308.

In vivo labeling of red blood cells utilizes intravenous injections of stannous ion followed by technetium-99m as the pertechnetate ion. This methodology has proven to be convenient and results in about 90% labeling efficiency (labeling efficiency refers to the percentage of available technetium-99m associated with red blood cells. The red blood cells labeled in vivo cannot, however, be used for blood volume measurements and spleen imaging.

Various methods for the in vitro labeling of red blood cells with technetium-99m have been disclosed in the literature; see, for example, J. Nucl. Med. Tech., 5: 32-34. The methods disclosed utilize a sterile pyrogen free container such as a plastic bag, partially evacuated collecting tube, or syringe.

U.S. Pat. No. 3,988,429 and J. Nucl. Med., 17: 126-132 disclose a relatively simple kit for the in vitro labeling of red blood cells. The kit disclosed is available commercially from Brookhaven National Laboratories. As disclosed in the patent, the amount of technetium-99m label used is limited.

BRIEF DESCRIPTION OF THE INVENTION

It is an object of this invention to provide a method for labeling red blood cells with technetium-99m.

It is a further object of this invention to provide a method for labeling red blood cells with high levels of technetium-99m activity.

It is a still further object of this invention to provide a method for labeling red blood cells which can utilize excess stannous ion as a reducing agent, thus facilitating manufacture.

The method of this invention comprises:

(i) mixing a blood sample with anticoagulant, stannous ion and buffer;

(ii) adding saline to the mixture;

(iii) centrifuging the mixture;

(iv) separating the supernatant from the red blood cells; and (v) mixing radioactive pertechnetate and an oxidizing agent with the red blood cells.

The kit of this invention comprises a reagent receptacle containing anticoagulant, stannous ion, and buffer, and a separate receptacle containing an oxidizing agent.

DETAILED DESCRIPTION OF THE INVENTION

The basic components of the kit of this invention are a reagent receptacle containing an anticoagulant, stannous ion and a buffer, and a separate receptacle containing an oxidizing agent.

It is preferred that the reagent receptacle be of the type that can be partially evacuated and used (in combination with a hypodermic needle) to sample a patient's blood. Such a receptacle eliminates the need for unnecessary manipulation of the blood sample and reagents. It is also preferred that the reagents contained in the reagent receptacle be lyophilized.

The particular anticoagulant used is not critical. The amount used will depend on the volume of blood to be sampled. Heparin is the preferred anticoagulant, and can, if desired, be used as a heparin salt (e.g., sodium heparin).

The buffer is used to stabilize the stannous ion in the solution against oxidation. Buffers are chosen based on their ability to protect the particular form of stannous ion used. Sodium citrate has been found to be particularly effective when stannous ion is present as stannous fluoride. The volume of buffer will be determined by the amount of stannous ion present in each kit.

Stannous ion can be present in the form of stannous fluoride, stannous pyrophosphate, stannous citrate, stannous chloride, stannous tartrate, or the like. As will be described more fully hereinafter, it has been found that a high labeling efficiency of red blood cells with technetium-99m can be achieved using an excess of stannous ion. The use of large amounts of stannous ion is, of course, highly desirable because without it, high labeling efficiency cannot be achieved at high levels of technetium-99m. Excess stannous ion also results in prolonged shelf life of the kit. The stannous ion should be present in an amount of not less than about 0.5 $\mu$g per ml of blood to be sampled. Preferably the stannous ion will be present in an amount of not less than about 1.0 $\mu$g per ml of blood to be sampled.

The second component of the kit is a receptacle containing an oxidizing agent. It is the oxidizing agent that permits the use of excess stannous ion without sacrificing labeling efficiency when red blood cells are labeled with technetium-99m. Although the mechanism is not clearly understood, it is thought that the red blood cells take up a fixed amount of stannous ion, and as the stannous ion in the kit is increased, more stannous ion remains outside the red blood cells. Labeling with technetium-99m (in the form of pertechnetate ion) is accomplished because the pertechnetate ion can cross the membrane of the red blood cells, be reduced inside of the cells and bind thereto. However, if the pertechnetate ion is reduced outside of the red blood cells (by excess stannous ions) it cannot cross the membrane of the red blood cells and binding cannot take place. The oxidizing agent is necessary, therefore, to prevent stannous ions not associated with red blood cells (i.e., not inside the red blood cells) from reducing the pertechnetate ion. Exemplary oxidizing agents which can be used in this invention are sodium hypochlorite, hydrogen peroxide, potassium iodate and the like; sodium hypochlorite is preferred.

In a preferred embodiment of this invention an antioxidant is added to the anticoagulant, stannous ion and buffer formulation to increase the shelf-life of the kit. Among the many antioxidants suitable for use in this invention are ascorbic acid, sodium sulfite, sodium thiosulfate and the like. Ascorbic acid is preferred. The amount of ascorbic acid used will preferably be five to ten times the amount of stannous ion in the kit.

The kit of this invention can optionally include a container of saline solution. As described hereinafter, saline solution is used in the process of this invention. However, its inclusion in the kit of this inventin is optional because many of the users of the kit will have saline solution available in their laboratories.

The method of this invention comprises first mixing a blood sample with a formulation comprising anticoagulant, stannous ion and buffer. It is preferred that the blood sampling and mixing be accomplished with a single receptacle. As described above, this is readily accomplished by supplying the formulation in a partially evacuated receptacle, which when coupled with a hypodermic needle can be used to obtain the necessary blood sample.

Saline solution is added to the mixture, and the mixture is shaken and centrifuged to pack the red blood cells. The saline solution dilutes the plasma and thus reduces the amount of plasma trapped in the cell fraction.

After centrifugation, the supernatant is separated from the red blood cells. This can be accomplished by withdrawing either the supernatant or the red blood cells from the receptacle. It is preferred that supernatant be withdrawn and discarded, and that the process continue in the same receptacle.

Labeling of the red blood cells is accomplished by mixing radioactive pertechnetate ion ($^{99m}TcO_4^-$) and oxidizing agent with the red blood cells. The radioactive pertechnetate ion is readily obtainable as a saline solution of radioactive sodium pertechnetate by elution of commercial generators with saline; see, for example, U.S. Pat. No. 3,920,995, issued Nov. 18, 1975.

The oxidizing agent and pertechnetate ion can be mixed first and then mixed with the red blood cells or they can be mixed with the red blood cells separately, without regard to which is added first.

The following is a preferred embodiment of the method of this invention:

(i) Draw patient's blood into a partially evacuated tube containing a lyophilized formulation comprising sodium heparin, stannous fluoride, sodium citrate, and ascorbic acid, and mix the contents gently.

(ii) Add saline solution to the tube (and withdraw the same volume of air to prevent pressure build-up in the tube) and rotate the tube a few times.

(iii) Centrifuge the tube.

(iv) Withdraw the supernatant and discard it.

(v) Add the necessary technetium-99m activity (as $Na^+TcO_4^-$) in saline solution to the receptacle and then add sodium hypochlorite to the solution. The receptacle is mixed gently for 5 minutes.

All components of the kit of this invention should be sterile. Furthermore, the method of this invention should be carried out using asceptic techniques.

The following example is a specific embodiment of this invention.

EXAMPLE

Preparation of kit

A first solution is prepared by dissolving 5 mg. of stannous fluoride in 1.0 ml of concentrated hydrochloric acid, and a second solution is prepared by dissolving 2.24 g of trisodium citrate ($Na_3C_6H_5O_7.2H_2O$) in 25 ml of nitrogen purged water. The first solution is added dropwise to the second solution, and 25 mg. of ascorbic acid is added to the resulting solution. The pH of the solution is adjusted to 6.0 using 1 N sodium hydroxide, and the volume of the solution is adjusted to 100 ml with water. To this solution is added 100 ml of sodium heparin (concentration is 1,000 U/ml) prepared by dissolving sodium heparin in normal saline.

The above-prepared solution is added to receptacles (e.g., Becton-Dickinson Vacutainer ®) in an amount of 0.2 ml, and lyophilized to dryness. Each receptacle contains 3.8 µg of stannous ion. The receptacles are stoppered at the appropriate level of vacuum to draw 6.0 ml of patient's blood. For each receptacle, a second receptacle is supplied containing 1.0 ml of a solution of sodium hypochlorite (0.025%) in normal saline.

Labeling of red blood cells

Blood (6.0 ml) from dogs is withdrawn directly into receptacles prepared as described above and the contents of each receptacle are gently mixed. Sodium chloride for injection (2.0 ml) is added aseptically to each receptacle and the same volume of air is withdrawn. The receptacles are rotated gently, and then centrifuged for 5 minutes at 2,000 rpm. The supernatant is withdrawn and discarded. The red blood cells in each receptacle are then labeled using 2.0 ml of labeling solution containing 1.0 mCi of technetium-99m and the entire contents of the second receptacle containing sodium hypochlorite is added to each. Mixing for 5 minutes completes the labeling procedure.

What is claimed is:

1. A method of labeling red blood cells with technetium-99m comprising:
   (i) mixing a blood sample with anticoagulant, stannous ion and buffer;
   (ii) adding saline to the mixture;
   (iii) centrifuging the mixture;
   (iv) separating the supernatant from the red blood cells; and
   (v) mixing radioactive pertechnetate and an oxidizing agent with the red blood cells.

2. A method in accordance with claim 1 wherein the anticoagulant is heparin or a salt thereof.

3. A method in accordance with claim 1 wherein the source of stannous ion is stannous fluoride or stannous pyrophosphate.

4. A method in accordance with claim 1 wherein the buffer is sodium citrate.

5. A method in accordance with claim 1 wherein the oxidizing agent is sodium hypochlorate.

6. A method in accordance with claim 1 comprising:
   (i) drawing a patient's blood into a partially evacuated tube containing a lyophilized formulation comprising anticoagulant, stannous ion and buffer;
   (ii) adding saline solution to the tube;
   (iii) centrifuging the tube
   (iv) withdrawing the supernatant from the tube;
   (v) adding radioactive pertechnetate ion and an oxidizing agent to the tube.

7. A method in accordance with claim 6 wherein the oxidizing agent is sodium hypochlorite.

8. A kit for use in the labeling of red blood cells with technetium-99m comprising a first receptacle containing an anticoagulant, stannous ion and a buffer, and a second receptacle containing an oxidizing agent.

9. A kit in accordance with claim 8 wherein the formulation in the first receptacle additionally comprises an antioxidant.

10. A kit in accordance with claim 8 wherein the first receptacle is partially evacuated and can be used in combination with a hypodermic needle to sample a patient's blood.

11. A kit in accordance with claim 8 wherein the formulation in the first receptacle is lyophilized.

12. A kit in accordance with claim 8 comprising a first receptacle containing heparin, or a salt thereof, stannous fluoride and sodium citrate and a second receptacle containing sodium hypochlorite.

13. A kit in accordance with claim 8 further comprising a third receptacle containing saline solution.

* * * * *

UNITED STATES PATENT AND TRADEMARK OFFICE
CERTIFICATE OF CORRECTION

PATENT NO. : 4,342,740
DATED : August 3, 1982
INVENTOR(S) : Rama K. Narra, et al.

It is certified that error appears in the above—identified patent and that said Letters Patent is hereby corrected as shown below:

Column 4, line 48, "hypochlorite" is misspelled.

Signed and Sealed this

Eighth Day of February 1983

[SEAL]

Attest:

GERALD J. MOSSINGHOFF

*Attesting Officer* — *Commissioner of Patents and Trademarks*